(12) United States Patent
Zapata Carrero et al.

(10) Patent No.: US 11,432,487 B2
(45) Date of Patent: Sep. 6, 2022

(54) SYSTEMS, METHODS AND KITS FOR MICROPROPAGATION OF CANNABIS

(71) Applicant: Front Range Biosciences, Inc., Boulder, CO (US)

(72) Inventors: Carmen Cecilia Zapata Carrero, Lafayette, CO (US); Carolina Sarmiento, Superior, CO (US); Jonathan David Vaught, Longmont, CO (US)

(73) Assignee: Front Range Biosciences, Inc., Boulder, CO (US)

( * ) Notice: Subject to any disclaimer, the term of this patent is extended or adjusted under 35 U.S.C. 154(b) by 0 days.

(21) Appl. No.: 17/050,940

(22) PCT Filed: May 10, 2019

(86) PCT No.: PCT/US2019/031759
§ 371 (c)(1),
(2) Date: Oct. 27, 2020

(87) PCT Pub. No.: WO2019/217843
PCT Pub. Date: Nov. 14, 2019

(65) Prior Publication Data
US 2021/0227764 A1 Jul. 29, 2021

Related U.S. Application Data

(60) Provisional application No. 62/670,198, filed on May 11, 2018.

(51) Int. Cl.
*A01H 6/28* (2018.01)
*A01H 4/00* (2006.01)

(52) U.S. Cl.
CPC ............. *A01H 4/005* (2013.01); *A01H 4/008* (2013.01); *A01H 6/28* (2018.05)

(58) Field of Classification Search
CPC ........... A01H 4/005; A01H 4/008; A01H 6/28
See application file for complete search history.

(56) References Cited

FOREIGN PATENT DOCUMENTS

| CN | 1887043 B | 8/2010 |
|---|---|---|
| CN | 107912301 A | 4/2018 |
| WO | 2019/217843 A1 | 11/2019 |

OTHER PUBLICATIONS

Pradhan S, Regmi T, Ranjit M, Pant B. Production of virus-free orchid Cymbidium aloifolium (L.) Sw. by various tissue culture techniques. Heliyon. 2016;2(10):e00176. Published Oct. 21, 2016. doi:10.1016/j.heliyon.2016.e00176 (Year: 2016).*
Reed, Barbara M., and Piyarak Tanprasert. "Detection and control of bacterial contaminants of plant tissue cultures. A review of recent literature." Plant tissue culture and Biotechnology 1.3 (1995): 137-142. (Year: 1995).*
Lata, H., et al. "In vitro propagation of *Cannabis sativa* L. and evaluation of regenerated plants for genetic fidelity and cannabinoids content for quality assurance." Protocols for In Vitro Cultures and Secondary Metabolite Analysis of Aromatic and Medicinal Plants, 2nd Edition. 2016. 275-288 (Year: 2016).*
Rahman, Shafkat Shamim. "DKW emerges as a superior media factor in vitro plant regeneration." Agri., 1 (1) (2018): 3-4 (Year: 2018).*
International Search Report and Written Opinion dated Jul. 10, 2019 in International Patent Application No. PCT/US2019/031759, filed on May 10, 2019, 21 pages.
International Preliminary Report on Patentability dated Nov. 26, 2020 in International Patent Application No. PCT/US2019/031759, filed on May 10, 2019, 15 pages.
Plant Tissue Culture Micropropagation is Growing, FI Biotech, Retrieved via http://www.f1biotech.com/article/detail/19/plant-tissue-culture-micropropagation-is-growing/, Dec. 26, 2017, 6 pages.
Biros Aaron G., "Applications for Tissue Culture in Cannabis Growing: Part 2", Cannabis Industry Journal, Retrieved via https://cannabisindustryjournal.com/feature_article/applications-for-tissue-culture-in-cannabis-growing-part-2/, May 3, 2017, 4 pages.
Chandra et al., "Assessment of Cannabinoids Content in Micropropagated Plants of Cannabis sativa and Their Comparison with Conventionally Propagated Plants and Mother Plant during Developmental Stages of Growth", Planta Medica, 2010, 76(7):743-750.
Chaohua et al., "A Rapid Shoot Regeneration Protocol from the Cotyledons of Hemp (*Cannabis sativa* L.)", Industrial Crops and Products, 2016, 83:61-65.
Culberson Eric, "A Primer on Tissue Culture", Cannabis Business Times, Retrieved via https://www.cannabisbusinesstimes.com/article/a-primer-on-tissue-culture/, Apr. 4, 2018, 3 pages.
Driver et al.,"In Vitro Propagation of Paradox Walnut Rootstock", HortScience, Aug. 1984, 19(4):507-509.
Lata et al., "Assessment of the Genetic Stability of Micro propagated Plants of Cannabis sativa by ISSR Markers", Planta Medica, 2010, 76:97-100.
Lata et al., "High Frequency Plant Regeneration from Leaf Derived Callus of High Δ9-Tetrahydrocannabinol Yielding *Cannabis sativa* L.", Planta Medica, 2010, 76:1629-1633.
Lata et al., "In Vitro Mass Propagation of *Cannabis sativa* L.: A Protocol Refinement Using Novel Aromatic Cytokinin Meta-Topolin and the Assessment of Eco-Physiological, Biochemical and Genetic Fidelity of Micropropagated Plants", Journal of Applied Research on Medicinal and Aromatic Plants, Mar. 2016, 3(1):18-26.
Lata et al., "In Vitro Propagation of *Cannabis sativa* L. and Evaluation of Regenerated Plants for Genetic Fidelity and Cannabinoids Content for Quality Assurance", Methods in Molecular Biology, Chapter 19, 2016, 1391:275-287.
Leifert et al., "Contaminants of Plant-Tissue and Cell Cultures", World Journal of Microbiology and Biotechnology, 1991, 7:452-469.

(Continued)

*Primary Examiner* — Weihua Fan
(74) *Attorney, Agent, or Firm* — Grant IP, Inc.

(57) ABSTRACT

Provided herein are systems, methods and kits for micropropagating disease-free cannabis plants, referred to as the Clean Stock® method. Also provided are Clean Stock® cannabis plants produced using such systems, methods and kits.

13 Claims, 1 Drawing Sheet

(56) References Cited

OTHER PUBLICATIONS

Murashige et al., "A Revised Medium for Rapid Growth and Bio Assays with Tobacco Tissue Cultures", Physiologia Plantarum, 1962, 15:473-497.
Stevens Michael J., "An Exclusive Look at Cannabis Tissue Culture, a Transformative Technology—Part 2", New Cannabis Ventures, Retrieved via https://www.newcannabisventures.com/an-exclusive-look-at-cannabis-tissue-culture-a-transformative-technology-part-2/, Oct. 11, 2016, 3 pages.
Tang Stephen, "Aurora Cannabis: Poised to Dominate Canadian Marijuana", Seeking Alpha, Retrieved via https://seekingalpha.com/article/4008996-aurora-cannabis-poised-to-dominate-canadian-marijuana, Sep. 28, 2016, 2 pages.

\* cited by examiner

Selected mother plants are placed in an environmentally controlled
greenhouse or clean space, monitored, allowed to grow, and virus tested.
Mother plants that test negative plant are used for initiation of tissue culture

Step 1: Nodal cuttings or Meristem Initiations (week 1)

Cuttings are taken from mother plants, stripped of all leaves, cut in ~1.5" sections, surface sterilized, and introduced into an establishment media without hormones (A) or with hormones (B). The initiated plant material is then placed in a vessel with agar nutrient rich media in a culture room and allowed to grow for ~4 weeks.

Step 2: Culture Indexing (~week 4)

After explants have differentiated and grown into plantlets, a culture indexing test is conducted to screen for bacterial contaminants by placing a portion of the explant in nutrient broth solution (C) for a week. The rest of the explant is introduced into multiplication media (B). Any explants that test positive for contamination are discarded.

Step 3: Multiplication (~week 5)

Plantlets that test negative for contamination are multiplied in multiplication media with hormones (B) or media for elongation (D) or (E), to allow for cell division and shoot proliferation.

Step 4: Rooted vs Unrooted (~week 9)

After the multiplication stage, plants are placed in rooting hormone media (F) or non-hormone media (A). Rooting can take ~4 weeks for plantlets to grow more vigorous, with larger leaf formation and a fully rooted base (rooted). Plantlets may be transferred directly from multiplication media into 72 cell plug trays in a greenhouse (unrooted).

Step 5: Hardening Off (~week 13)

The last step of micropropagation is to release the plants from the lab environment into a greenhouse. Plants may be growing in hormone rooting media (F) or non-hormone media (A) prior to transfer.

SYSTEMS, METHODS AND KITS FOR MICROPROPAGATION OF CANNABIS

RELATED PATENT APPLICATION(S)

This application is a 35 U.S.C. 371 national phase patent application of PCT/US2019/031759 filed on May 10, 2019, entitled "SYSTEMS, METHODS AND KITS FOR MICROPROPAGATION OF CANNABIS," naming Carmen Cecilia ZAPATA CARRERO et al. as inventors, which claims priority from U.S. provisional application No. 62/670,198, filed May 11, 2018, each herein incorporated by reference in its entirety.

FIELD

The disclosure relates to systems, methods, and kits for tissue culture production of disease-free cannabis plants.

BACKGROUND

Cannabis is a genus of flowering plants that includes at least three species, *Cannabis sativa, Cannabis indica*, and *Cannabis ruderalis*, as determined by plant phenotypes and secondary metabolite profiles (chemotype). Both marijuana and hemp plants are in this genus and produce a unique family of terpeno-phenolic compounds called cannabinoids. The cannabinoids typically produced in greatest abundance are cannabidiol (CBD) and $\Delta^9$-tetrahydrocannabinol (THC). CBD and THC have been shown to have different physiological effects when ingested. Cannabis is used to produce hemp fiber and hemp oil, for medicinal purposes, and as a recreational drug. Hemp cultivars of Cannabis are bred to produce minimal levels of THC, while marijuana cultivars are bred to produce higher levels of THC. CBD has been shown to have a number of medically useful effects such as anti-inflammatory, anti-convulsant, antioxidant, antiemetic, anxiolytic and antipsychotic effects, and THC is psychoactive. In general, the maximum THC content of hemp is 0.3% and any cannabis with a THC content of greater than 0.3% is considered to be marijuana.

Given these differences between hemp and marijuana, cannabis consumers want to know the relative levels of THC and CBD in the cannabis they are purchasing and consuming and are therefore interested in plant products that have a known and consistent phenotype and chemotype. In addition, cannabis consumers want to know that a hemp or marijuana product does not contain pesticides. Cannabis growers need to be able to provide consistent disease-free hemp and marijuana plants to consumers and to be able to carry out large scale cost-effective propagation of such plants.

Cannabis growers desire to select hemp and marijuana plants with a favorable physiological "phenotype" and chemical profile "chemotype". In general, growers use vegetative propagation (or vegetative cloning) to multiply plants starting with a "mother" plant by way of "cuttings", using a small branch of the mother plant and rooting the branch to produce new "daughter" plants.

Vegetative propagation without first "cleaning" the mother plant has limitations, including the transfer of disease to the next generation resulting in inferior plant quality and yield, which can limit the number of plants that can be generated, and difficulty in maintaining consistency in successive generations because mother plants that donate their cuttings in the vegetative propagation process are not immortal. A grower may find a mother plant with highly desirable characteristics but be unable to preserve its genetic properties. In addition, plants may become infected with bacterial, fungal and viral pathogens, and in response growers typically apply pesticides to minimize plant damage and loss of yield.

A number of commercial plants are propagated using tissue culture, including sugarcane, grape, strawberry, bamboo, and orchids, for example to remove pathogens. At present, no pesticide product is federally registered for use on cannabis, and the states of Colorado, Washington and Oregon have discovered that after legalizing cannabis and implementing regulatory oversight at the state level, a surprising percentage of cannabis plants contain pesticide residue. This has resulted in recalls and public-safety alerts. Growers may believe that if a mother plant was treated with pesticides daughter plants produced by vegetative propagation will be pesticide-free, however, if a pesticide causes systemic contamination, it can persist for a long time and be passed on by vegetative propagation.

In addition, cannabis consumers want to know the relative levels of THC and CBD in the cannabis they are purchasing and ingesting and are therefore interested in plant products that have a consistent phenotype and chemotype and do not contain pesticideresidue.

Cannabis growers need to be able to provide consistent, pesticide- and disease-free hemp and marijuana plants to consumers and to be able to carry out large scale cost-effective propagation of such plants.

There is a need for improved starter plants for propagation of cannabis, that are disease-free without application of pesticides, characterized in terms of desirable and stable phenotype and chemotype, and which are capable of multiplication to produce large numbers of clonal plants.

The systems and methods described herein meet the needs of cannabis consumers and growers.

SUMMARY

The disclosure provides systems and methods for in vitro propagation of disease-free clonal cannabis plants.

The disease-free clonal cannabis plants may be true-to-type and have the chemotype of a marijuana cultivar.

The disease-free clonal cannabis plants may be true-to-type and have the chemotype of a hemp cultivar.

The clean explant may be one or more of meristematic tissue, an apical explant, a nodal explant, root tips, shoot tips, young stems and young leaves.

The mother plant may be a virus-tested and culture-indexed mother plant.

The system and methods may be effective to produce at least 200× the number of starting explants or from 30 to 3072 clonal disease-free cannabis plants within 15 to 17 weeks following day 0.

The system and methods may be effective to produce at least 1000× the number of starting explants within 15 to 17 weeks following day 0.

The disclosure further provides methods of producing disease-free clonal cannabis plants by micropropagation of an explant from a mother cannabis plant. Such methods in some examples include, a tissue culture initiation stage; a culture indexing step; a micropropagation stage; a pre-rooting or rooting stage; and a hardening off stage, wherein the method is effective to produce a number of disease-free clonal cannabis plants that is at least 200× the number of starting explants within 15 to 17 weeks of initiation of the culture. For example, such a method can include initiating tissue culture from an explant of a mother cannabis plant;

performing culture indexing; micropropagating the explant; pre-rooting or rooting the explant; and acclimatizing the explant, wherein the method is effective to produce a number of disease-free clonal cannabis plants that is at least 200 times (200×) the number of starting explants within 15 to 17 weeks of initiation of the culture.

Kits for commercial propagation of disease-free clonal cannabis plants are also provided.

BRIEF DESCRIPTION OF THE DRAWING

FIG. 1 is a schematic depiction of the steps in an exemplary process for micropropagation of cannabis.

It should be appreciated that the constructions and properties illustrated in FIG. 1 is a specific example and not intended to limit the scope of constructions and testing that may be used. Other materials, constructions and sequences of steps may also be performed according to alternative embodiments. For example, alternative embodiments may contain additional methods, steps, reagents, timeframes and environmental conditions. One of ordinary skill in the art would recognize and appreciate that there are many variations, modifications, and alternatives to the constructions.

DETAILED DESCRIPTION

The specification and drawing are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed embodiments are susceptible to various modifications and alternative constructions, one illustrated embodiment thereof is shown in the drawing and others are described herein. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

All patents, publications, and patent applications cited in this specification are herein incorporated by reference as if each individual patent, publication, or patent application was specifically and individually indicated to be incorporated by reference in its entirety for all purposes.

Unless defined otherwise, all technical and scientific terms used herein have the same meaning as commonly understood by one of ordinary skill in the art to which the disclosure pertains. Although other methods and materials, similar or equivalent to those described herein can be used in the practice of the present disclosure, exemplary materials and methods are described herein.

In describing and claiming the present invention, the following terminology will be used in accordance with the descriptions below.

As used herein, the term "asexual propagation" means reproducing plants using the following methods: cuttings, layering, division, grafting, budding and tissue culture. Asexual propagation does not involve exchange of genetic material and almost always produces plants that are identical to a single parent.

The term "cannabis", is used with reference to a genus of flowering plants in the family Cannabaceae, which contains at least 3 species: *Cannabis sativa*, *Cannabis indica*, and *Cannabis ruderalis*.

As used herein, the term "Clean Stock®" is used with reference to plants grown in accordance with a set of practices provided herein designed to make them free of economically important pathogens as determined by stated procedures and are true to type.

As used herein, the term "cleaning" is the process of removing one or more contaminants from a plant. If the contaminant is a pathogen exemplary methods include one or more of thermotherapy of meristems, chemotherapy, meristem-tip culture, and use of chemicals in the media.

As used herein, the term "clone" means progeny of an individual plant produced asexually. A clone is typically a "copy" of the parent or "mother" plant. For avoidance of doubt, the term "clone" may be used to describe cannabis plants produced by "traditional" vegetative propagation; however, progeny plants produced by vegetative propagation of uncleaned plants differ from the Clean Stock® clones described herein.

As used herein, the term "commercial production" is the last stage of production that increases numbers of plants, e.g., in a Clean Stock® system provided herein. Plants from this build-up phase are sent to growers for planting, for example in commercial fields, greenhouses or grow rooms.

As used herein, the term "cultivar" is plant or group of plants (e.g., a variety) cultivated by humans and selected for desirable characteristics. Although some cultivars can occur in nature as plant mutations, most cultivars are developed by plant breeders, i.e., as hybrids of two plants. To propagate true-to-type clones, many cultivars can be propagated vegetatively (e.g., through cuttings, grafting, or tissue culture), not propagation by seed.

As used herein, the term "culture indexing" means the testing of an individual plant cutting by sampling and placing stem sections into an all-purpose enriched media, designed to grow bacteria and fungi. Growth of bacteria and fungi is easily observed when the media becomes cloudy. The plant/cutting associated with such growth is discarded. Explants associated with clean cultures are considered to be "culture-indexed".

As used herein, the term "cutting" means a section of a plant that is the starting material for vegetative propagation.

The term "disease-free" is used with reference to plants that have been screened for certain viruses, bacteria, and fungi, determined to be "clean", and maintained under controlled conditions without use of pesticides. Thus, in some examples disease-free is used to refer to plants that are determined to be "virus-free" and "free of bacteria and fungi". For example, a culture can be determined to be "free of bacteria and fungi" using a culture indexing test. In some examples, such a method includes culturing for about 7 days in Leifert and Waites Solution, then visually inspecting the culture for turbidity, an indication of microbial contamination (See, e.g., Leifert, Ritchie and Waites, World Journal of Microbiology and Biotechnology 7:452-469, 1991). Cultures having any observable turbidity are removed and those pants are discarded. For example, a culture can be determined to be free of viruses using PCR. In some examples, "virus-free" is indicated whenthe plants do not product a positive test result for any of the following viruses, for example using PCR or ELISA methods:

| | |
|---|---|
| Arabis Mosaic Virus | ArMV |
| Tobacco Mosaic Virus | TMV |
| Cucumber Mosaic Virus | CMV |
| Alfalfa Mosaic Virus | AMV |
| Tomato Ringspot Virus | ToRSV |

-continued

| Tobacco streak Virus | TSV |
| Tobacco Ringspot Virus | TRSV |
| Potyvirus Group | POTY |

As used herein, the term "Elite Nucleus Mother Plants" is used with reference to mother plants sourced directly from a Clean Stock® program and grown in facilities under conditions to ensure optimal plant health with on-going evaluation under optimal growing conditions favoring normal vegetative and reproductive growth for true to type (TTT) evaluations.

As used herein, the term "environmental conditions" with respect to tissue culture means light, temperature, humidity, and tissue culture medium comprising a specified pH and concentration of growth factors.

The term "explant", used herein with reference to plant tissue culture, means living plant tissue that is removed from the natural site of growth and placed in sterile medium (e.g., DKW or MS) for culture. This can be of any tissue type such as leaves, roots, stems, or any portion taken from a plant and used to initiate tissue culture.

As used herein, the term "footbath" is a container of disinfectant that sits just inside a greenhouse entry filled with approved disinfectant into which the soles of shoes are immersed prior to entering the area. Shoes are brushed off at the entrance prior to using the footbath. Footbaths are kept clean and typically renewed daily.

As used herein, the term "generation 1 (G1)" refers to an original mother plant ("nuclear material") that is tested for viruses (e.g., using PCR) and maintained in isolation in a "Nucleus Block" in order to prevent contamination. G1 stock is the original source of virus-tested "clean" plant material that is distributed to nurseries, growers or other interested parties within certification programs, such as those for grapes and fruit and nut trees.

As used herein, the term "generation 2 (G2)" refers to plant material propagated from G1 stock and grown under specific conditions to prevent contamination. G2 stock is frequently maintained by nurseries for supply to commercial growers.

As used herein, the term "generation 3 (G3) and Generation 4 (G4)" refers to plant material propagated from G2 and G3 stock, respectively.

As used herein, the terms "generation G2, G3, G4, etc." are generational designations for each propagation level derived from a G1, original pathogen-tested plant.

As used herein, the term "hardening off" means the transfer of tissue-culture produced plantlets (plants) from tissue culture media and an incubator environment with controlled environmental conditions to soil in a greenhouse.

The term "heat treatment" is used herein with reference to thermotherapy.

As used herein, the term "hemp", typically means a cultivar of cannabis that has a THC content of 0.3% or less.

As used herein, the term "initiation" is the tissue culture phase where explants are taken and placed into in vitro conditions in preparation for culture indexing and multiplication.

As used herein, the term "initiation date" is the date of explant initiation. Each clonal initiation carries an initiation date along with the source plant information for identification and trace-back purposes.

As used herein, the term "marijuana", means a cultivar of cannabis that has a THC content of greater than 0.3%.

As used herein, the term "meristem", means a region of specialized tissue whose cells undergo cell division. The cells of meristems typically have thin walls, prominent nuclei and small vacuoles.

As used herein, the term "meristem tip (tissue) culture" is a plant propagation or disease elimination technique where tissue pieces are separated from a mother plant and cultured in a sterile growth medium apart from the source plant.

As used herein, the term "micropropagation" is the practice of rapidly multiplying plant material to produce a large number of progeny plants (clones) using plant tissue culture methods. Micropropagation is used to multiply commercially useful plants, such as those that have bred through conventional plant methods or been genetically modified. It is also used to provide plantlets from a stock plant which does not produce seeds or for which vegetative reproduction is not commercially viable.

As used herein, the term "micropropagation stage" means a stage of plant tissue culture that has a duration of about 3-4 weeks, where the plant growth media is DKW or Murashige and Skoog salts standard media (MS), and may include vitamins, plant hormones such as benzylaminopurine (BAP), thidiazuron (TDZ), meta-topolin (mT), gibberellic acid (GA3), and indole butyric acid (IBA).

The term "mother plant", is used with reference to a selected young heathy plant exhibiting a desired phenotype and chemotype, which is typically maintained in a vegetative stage throughout its life and has passed rigorous testing for diseases as required by a Clean Stock® program. These plants provide clean true to type explants to begin the production of clean commercial plants.

As used herein, the term "Murashige and Skoog salts standard media" or "MS", means Murashige and Skoog salts standard media plus vitamins, as described in "Murashige T & Skoog F. A revised medium for rapid growth and bioassays with tobacco tissue cultures. Physiol. Plant. 15:473-97, 1962".

As used herein, the term "Nucleus House" is a greenhouse or screen house with special structural and sanitation requirements which will house the G1 or nucleus plants.

As used herein, "nucleus or certification stock" is a planting of a group of mother plants from sources that have been tested for viruses or other diseases and are maintained in isolation under conditions that prevent (re)infection.

As used herein, the term "off type" means any plant that for any reason is not true to type (TTT).

The term "pathogen" is used herein with reference to a microorganism causing disease. Examples of pathogens include viruses, viroids, bacteria, fungi, and phytoplasmas.

The term "pest" is any species, strain or biotype of plant, animal or pathogenic agent injurious to plants or plant products.

As used herein, the term "plant growth media" or "plant tissue culture media", means sterile liquid, semi-solid, or solid media containing nutrients and other ingredients.

As used herein, "plant quarantine" is used with reference to all activities designed to prevent the introduction and/or spread of pests and pathogens.

As used herein, the term "plantlet" means young or small plants. The terms "plantlet" and "plant" may be used interchangeably herein as in tissue culture all plants are "plantlets".

The term "screen house" is used herein with reference to a house with insect proof screen for much of the walls that allows for the maximum air movement for temperature control. Fans may be used for air exchange and/or circulation. A screen house is used to house living plant material under secure conditions which minimize the risk of disease introduced by insects or pollen from the outside environment.

The term "shoot-tip culture" is used herein with reference to the placing into plant tissue culture a small piece of tissue from the meristematic region that is typically greater than about 1 mm in length.

As used herein, the term "somaclonal variation" means the variation seen in plants that have been produced by plant tissue culture. The variations can be genotypic or phenotypic, which in the latter case can be either genetic or epigenetic in origin. Typical genetic alterations are changes in chromosome numbers (polyploidy and aneuploidy), chromosome structure (translocations, deletions, insertions and duplications) and DNA sequence (base mutations).

As used herein, the term "thermotherapy" refers to a process of maintaining living plants in a chamber or room where light and temperature can be manipulated throughout a 24-hour time period, typically providing long days of light and temperatures near 100° F. for at least 16 hours and typically a lower temperature (such as 25 to 40° C.) during the dark period. Often the conditions are adjusted as appropriate to maintain the genetics of the plant being treated with the goal of causing virus escape when explants are removed from the plants after the heating period.

The term "tissue culture", as used herein refers to the growth of tissues or cells separate from the organism. This is typically facilitated via use of a liquid, semi-solid, or solid growth medium, such as broth or agar.

As used herein, the "tissue culture initiation stage" means a stage of plant tissue culture that typically has a duration of about 3-4 weeks, wherein the plant growth media may be MS plus vitamins.

The term "trueness to type", "true to type", or "TTT", is used to describe a plant or group of plants of a particular cultivar which has a heritable phenotype and chemotype. TTT plants exhibit no noticeable variation in phenotype under specified environmental conditions For example, the height, color, leaf morphology, leaf color, time to flower, and the like. A plant cultivar that is not TTT could be a mixture of cultivars in a population or a phenotype and chemotype that is not stable and exhibits noticeable changes in phenotypic attributes.

The term "vegetative propagation", as used herein refers to asexual plant reproduction.

The term "virus indexing" as used herein refers to testing of plants for the presence of specific viruses using one or more of various methods and tracking the tests to certain plant unique identifications. Once tested thoroughly by the disclosed Clean Stock® method, the plant in considered a 'virus-indexed plant.'

The term "young explants" with respect to a mother plant means explants taken from a mother plant that is from 2 to 8 months of age.

In the following description, various embodiments of the disclosure will be described. For purposes of explanation, specific configurations and details are described in order to provide a thorough understanding of the embodiments. However, it will also be apparent to those skilled in the art that the embodiments may be practiced without the specific details. Furthermore, well-known features may be omitted or simplified in order not to obscure the embodiment being described.

Overview

Current systems and methods for propagating Cannabis largely rely on vegetative propagation using vegetative cuttings to produce as many "daughter" plants as possible. This approach has numerous limitations that are a deterrent to the large-scale production of healthy, disease-free cannabis plants needed for commercial production.

Through extensive experimentation and evaluation, the inventors have developednew, useful, and cost-effective systems and methods for micropropagation and largescale propagation of disease-free (e.g., "free of bacteria and fungi" and "virus-free", as determined using culture indexing and PCR or ELISA, respectively) cannabis plants. The Clean Stock® program described herein minimizes the incidence of infectious disease in a nursery supply chain, assure true to type nature and traceability of nursery propagated plants, and to facilitate germplasm exchange.

As detailed herein, the use of tissue culture cloning (micropropagation) to produce disease-free and pest-free "Clean Stock®" hemp and marijuana plants that are clones of a mother plant with a desired phenotype and chemotype significantly reduces disease risk, improves the plant production yield and requires significantly less space and labor than propagation using vegetative cuttings. In addition, tissue culture propagation methods and systems described herein provide a means to archive a cultivar (also referred to as a varietal) with a selected phenotype and chemotype in a genetic bank essentially indefinitely. The tissue culture repository of a varietal of interest may be multiplied and propagated to yield large number of plants upon demand.

Mother plants pass a comprehensive virus test (typically using PCR) and be culture indexed, with regular follow-up testing. Mother plants and clonal lines are uniquely named and traced throughout the propagation process in the laboratory and in the greenhouse.

In one embodiment, selection of a mother plant for the disclosed Clean Stock® program includes selecting at least two plants from a cultivar of interest that are true to type (TTT), testing the plants to ensure that they are virus-free (such as free from ArMV, TMV, CMV, AMV, ToRSV, TSV, TRSV and POTY), initiate in tissue culture and perform culture indexing. After it has been determined that the candidate mother plant is virus free and yields a negative result in the culture indexing process, source material for tissue culture is taken from the plant. The plants produced from tissue culture micropropagation of such plants provide a source for preservation of cannabis cultivars having a desired phenotype and chemotype and are optimal starter plants for large scale propagation.

Systems

Disclosed herein are systems for in vitro and in vivo propagation of disease-free cannabis plants. The plants produced from such systems provide a source for preservation of cannabis cultivars having a desired phenotype and chemotype and are optimal starter plants for large scale propagation of cannabis.

Disease-free cannabis plants are generated from a mother plant with a desired phenotype and chemotype that has been maintained in a vegetative state throughout its life. In some embodiments, the mother plant has an age of from 1 to 4 months, from 2 to 6 months, or from 3 to 5 months, e.g., from 1 to 1.5 months, from 1.5 to 2 months, from 2 to 2.5 months, from 2.5 to 3 months, from 3 to 3.5 months, from 3.5 to 4 months, from 4 to 4.5 months, from 4.5 to 5 months, from 5 to 5.5 months, from 5.5 to 6 months, from 6 to 6.5 months, 6.5 to 7 months, from 7 to 7.5 months or from 7.5 to 8 months.

A mother plant which serves as a source of tissue culture explants is tested for viruses and maintained under conditions that prevent infection or re-infection. Generation 1 (G1) mother plants are the source of virus-tested plant material and provide clean true to type plants to begin the production of disease-free commercial plants.

In some embodiments, the tissue culture system relies on explants taken from one or more of meristematic tissue, an apical explant, a nodal explant, a root tip, a shoot tip, a young stem or young leaves for initiation of tissue culture.

In some embodiments, the tissue culture system further includes an incubator or other chamber comprising controlled environmental conditions effective to produce disease-free cannabis plants. Such environmental conditions comprise exposing said explants to various tissue culture media under aseptic conditions with controlled light intensity, photoperiod, temperature, humidity, and media pH.

A CleanStock® plant may be used as the "mother plant" to multiply plant material, serve as a source of plant material for generating derivative lines; breeding; generating crosses; evaluating or preserving phenotypic and chemotypic characteristics and/or genetics; production of: seeds, liners, crosses, rooted or non-rooted cuttings, rooted or non-rooted clones or pollen: biomass including but not limited to flower, extracted oil, and other processed plant material.

Methods

Methods and systems for in vitro propagation of CleanStock® disease-free cannabisplants rely on micropropagation of explants taken from mother plants with desired phenotypes, chemotypes, and/or genotypes that can provide clean true to type explants and serve as a starting point for the production of clean commercial plants.

Micropropagation typically includes 5 stages or steps. The method includes preparing and selecting virus-free healthy mother plants having desired phenotypes, chemotypes, and/or genotypes. In some examples, a virus-free mother plant is free from ArMV, TMV, CMV, AMV, ToRSV, TSV, TRSV and POTY, for example as determined using PCR or ELISA. In some embodiments, mother plants are asexually propagated in a greenhouse or screen house with special structural and sanitation requirements, e.g., for up to about 10 weeks.

Avoiding and preventing microbial contamination of plant tissue culture is critical to successful micropropagation. Bacterial contamination can be visually inspected at the base of the plant in a vessel, but further screening is necessary to assure that plant is free of any slow growing bacteria, endophytes and bacteria that do not grow on plant tissue culture media. The process of culture indexing can detect bacteria by slicing section of the explant and inoculating in nutrient film broth solution. This can be repeated at various stages in the micropropagation process to ensure further quality control. Plant material is also screened for the presence of discoloration and insects by checking under the leaves and every surface of the plant. Only healthy plants are used to initiate tissue culture micropropagation of cannabis.

An exemplary tissue culture micropropagation process for cannabis is illustrated in FIG. 1.

In some embodiments, step 1 of the method includes meristem or node initiation, and introduction and establishment of aseptic culture using media A or B (described in Table 1, below).

In one embodiment, explants are taken from a G1 mother plant and placed in contact with tissue culture media in vitro under aseptic conditions on day 0. In some embodiments, meristems from about 0.5 to 0.7 mm in length, are used to initiate the culture. In some embodiments, a shoot tip that is between 0.5 and 0.7 mm in length is used to initiate tissue culture of cannabis. In some embodiments, nodal cuttings or apical tips from 2 cm to 3 cm, 2 cm to 4 cm, or 1 cm to 5 cm in length with approximately 0.5 cm to 2.0 cm, 0.75 cm to 1.5 cm, or 1 cm to 1.5 cm of stem below the lowest node are used to initiate tissue culture of cannabis. In some embodiments, a cutting that is shorter or longer than 1 cm to 5 cm in length is used to initiate tissue culture of cannabis. In some embodiments, the initiation step or stage takes about one week, with establishment of in vitro plants in about 3 to 7 weeks, 4 to 6 weeks, or 4 to 5 weeks.

In some embodiments, MS medium plus vitamins is used to initiate culture of the explant. In some embodiments In one exemplary embodiment, an explant is cultured in an incubation chamber under aseptic conditions with a light intensity of about 60 umol/m2/s, a controlled photoperiod, a temperature of 22-25° C., 100% humidity, and tissue culture media with a pH of 5.7 before autoclaving, under conditions effective to multiply the explant.

In some embodiments, a method for tissue culture propagation of cannabis includes Step 2, "culture indexing", which may be conducted at periodic intervals and provides a screen for bacterial, fungal, and other contaminants in a nutrient broth typically used by those of skill in the art to culture bacteria or fungi. In this step, tissue culture media comprising explants is screened for contamination and any contaminated cultures are removed. Explants associated with clean cultures are considered to be "culture-indexed". In some embodiments, Step 2 relies on use of media B for plants and C (described in Table 1, below), for contaminant screening.

In some embodiments, a method for tissue culture propagation of cannabis includes Step 3, "lab micropropagation", wherein "clean" cannabis explants are transferred to proliferation media, such that they can be divided and multiplied. This stage serves to generate large numbers of shoots per explant. In some embodiments, the micropropagation step lasts three or more weeks and relies on use of media B and/or D (described in Table 1, below), as the micropropagation medium. In one exemplary embodiment, the micropropagation step comprises transfer of a nodal or apical cutting of about 1.5 cm in length to fresh micropropagation media.

In some embodiments, a method for tissue culture propagation of cannabis includes Step 4, "lab rooting". In some cases, "lab-rooting" comprises, "unrooted in vitro plants". In some cases, lab-rooting" comprises, a "pre-rooting stage". The timeframe for this stage will vary dependent upon which method is employed.

In some embodiments, the method includes, an "unrooted in vitro plant" step wherein rooted plantlets are established in rooting media. In some examples of this embodiment, a pre-rooting stage (induction of rooting) is employed wherein rooted plantlets are established in 72 cell plug trays in a greenhouse. Use of a pre-rooting stage instead of a rooting stage can reduce the rooting cycle by 2 or more weeks. In some embodiments, Step 4 relies on use of media A or E (described in Table 1, below).

In some embodiments, a method for tissue culture propagation of cannabis includes Step 5, "acclimatization", wherein plantlets are transferred to soil for growth in a greenhouse. This may be followed by large scale propagation of CleanStock® plants, as further detailed below.

Tissue Culture Media

Plant growth media for use in tissue culture micropropagation of cannabis is (sterile) liquid, semi-solid, or solid media and contains nutrients and other reagents.

In some embodiments, the initial and maintenance medium tissue culture growth media for cannabis is Murashige and Skoog salts plus vitamins (MS), a standard mixture of specific nutrients developed for plant tissue culture (Murashige T & Skoog F). A revised medium for rapid growth and bioassays with tobacco tissue cultures. Physiol. Plant. 15:473-97, 1962), expressly incorporated by reference herein. MS salts and vitamins are available pre-mixed from many sources. In some embodiments, MS media is modified and/or supplemented. In some embodiments, the medium tissue culture growth media for cannabis is Driver and Kuniyaki Walnut (DKW) media (Driver J A, Kuniyuki A H, 1984, In vitro propagation of Paradox walnut rootstock. Hortscience 19:507-509), expressly incorporated by reference herein.

In some embodiments, plant hormones such as benzylaminopurine (BAP), thidiazuron (TDZ), meta-topolin (mT), gibberellic acid 3 (GA3), and Indole Butyric Acid (IBA) are included in the tissue culture media.

In some embodiments, one more of, benzylaminopurine (BAP) (such as a concentration of from 0.01-2 mg/L); thidiazuron (TDZ) (such as a concentration of from 0.05-0.5 mg/L); meta-topolin (mT) (such as s concentration of from 0.1-0.5 mg/L); gibberellic acid 3 (GA3) (such as a concentration of from 0.3-1 mg/L); and Indole Butyric Acid (IBA) (such as a concentration of from 0.1-1 mg/L) are included in the tissue culture medium.

In some embodiments, the plant growth media used in the pre-rooting/induction/elongation stage of cannabis tissue culture is "DKW Basal media" plus vitamins. In some embodiments, woody plant media is modified and/or supplemented.

In some embodiments, plant hormones may be included in plant growth media for pre-rooting/induction/elongation of cannabis plantlets, e.g., IBA, which may be provided at a concentration of from 0.8-2 mg/L.

TABLE 1

Tissue Culture Media.

| Week MEDIA | PURPOSE | STEP # |
|---|---|---|
| A | Establishment Media (MS) | 1 |
| B | Micropropagation Media (DKW Basal Media) with/without Hormones | 1, 2, 3 |
| C | Nutrient Broth Solution | 2 |
| D | Media for Elongation (DKW Basal Media plus vitamins, and hormones include IBA 0.1-3 mg/L and GA3 0.4-1.5 mg/L) | 3 |
| E | Rooting Media (DKW Basal Media plus vitamins and include 0.5-2.00 mg/L IBA) | 4 |

Yield from Micropropagation of Cannabis

In some embodiments, within 15 to 17 weeks following initiation of tissue culture with a cannabis explant (day 0), the number of clonal disease-free cannabis plants produced using the systems and methods described herein is at least 200 times (200×), at least 210×, at least 220×, at least 230×, at least 240×, at least 250× or at least 256× the number of starting explants, as detailed in Table 2.

As shown in Table 2, within 17 weeks following initiation of tissue culture with a cannabis explant, the systems and methods described herein are effective to produce at least 30 to 1536 clonal disease-free cannabis plants when tissue culture is initiated with 6 explants, at least 45 to 2304 clonal disease-free cannabis plants when tissue culture is initiated with 9 explants, or at least 60 to 3072 clonal disease-free cannabis plants when tissue culture is initiated with 12 explants.

TABLE 2

Exemplary Yield from Micropropagation of Cannabis.

| | Starting with 6 plants/vessel Propagation Factor | | | Starting with 9 plants/vessel Propagation Factor | | | Starting with 12 plants/vessel Propagation Factor | | |
|---|---|---|---|---|---|---|---|---|---|
| WEEK | 1.5 | 2 | 4 | 1.5 | 2 | 4 | 1.5 | 2 | 4 |
| 1 | 6 | 6 | 6 | 9 | 9 | 9 | 12 | 12 | 12 |
| 5 | 9 | 12 | 24 | 13 | 18 | 36 | 18 | 24 | 48 |
| 9 | 13 | 24 | 96 | 20 | 36 | 144 | 27 | 48 | 192 |
| 13 | 20 | 48 | 384 | 30 | 72 | 576 | 40 | 96 | 768 |
| 17 | 30 | 96 | 1536 | 45 | 144 | 2304 | 60 | 192 | 3072 |

In some embodiments, within 15 to 17 weeks following initiation of tissue culture with a cannabis explant (day 0), the number of clonal disease-free cannabis plants produced using the systems and methods described herein is at least 4000 times (4000×), at least 4020×, at least 4040×, at least 4060×, at least 4080λ, or at least 4096× the number of starting explants, as detailed in Table 3.

As shown in Table 3, within 17 weeks following initiation of tissue culture with a cannabis explant, the systems and methods described herein are effective to produce at least 30 to 24576 clonal disease-free cannabis plants when tissue culture is initiated with 6 explants, at least 45 to 36864 clonal disease-free cannabis plants when tissue culture is initiated with 9 explants, or at least 60 to 49152 clonal disease-free cannabis plants when tissue culture is initiated with 12 explants.

TABLE 3

Exemplary Yield from Micropropagation of Cannabis.

| | Starting with 6 plants/vessel Propagation Factor | | | | Starting with 9 plants/vessel Propagation Factor | | | | Starting with 12 plants/vessel Propagation Factor | | | |
|---|---|---|---|---|---|---|---|---|---|---|---|---|
| WEEK | 1.5 | 2 | 4 | 8 | 1.5 | 2 | 4 | 8 | 1.5 | 2 | 4 | 8 |
| 1 | 6 | 6 | 6 | 6 | 9 | 9 | 9 | 9 | 12 | 12 | 12 | 12 |
| 5 | 9 | 12 | 24 | 48 | 13 | 18 | 36 | 72 | 18 | 24 | 48 | 96 |

TABLE 3-continued

Exemplary Yield from Micropropagation of Cannabis.

| | Starting with 6 plants/vessel Propagation Factor | | | | Starting with 9 plants/vessel Propagation Factor | | | | Starting with 12 plants/vessel Propagation Factor | | | |
|---|---|---|---|---|---|---|---|---|---|---|---|---|
| WEEK | 1.5 | 2 | 4 | 8 | 1.5 | 2 | 4 | 8 | 1.5 | 2 | 4 | 8 |
| 9 | 13 | 24 | 96 | 384 | 20 | 36 | 144 | 576 | 27 | 48 | 192 | 768 |
| 13 | 20 | 48 | 384 | 3072 | 30 | 72 | 576 | 4608 | 40 | 96 | 768 | 6144 |
| 17 | 30 | 96 | 1536 | 24576 | 45 | 144 | 2304 | 36864 | 60 | 192 | 3072 | 49152 |

Kits

The systems and methods described herein may be used to produce material for a kit for commercial propagation of cannabis. Such kits may include one or more of starting plant material from disease-free hemp or marijuana plants, tissue culture medium, and instructions for micropropagation.

Large Scale Propagation of Cannabis

In some embodiments, Clean Stock® plants are acclimatized in the greenhouse and transferred to soil to produce mother plants which may be used to generate cuttings that are rooted and grown for various purposes, as detailed hereinabove.

Methods and systems for in vitro propagation of "cleaned" disease-free cannabis plants rely on propagation of cuttings taken from mother plants with desired phenotypes, chemotypes, and/or genotypes that can provide clean true to type plants and serve as a starting point for the large-scale production of clean commercial cannabis plants.

Numerous factors impact the yield from large scale production of cannabis, including but not limited to temperature, humidity, the spectrum of light and its source, nutrients, soil profile including pH, $CO_2$ levels, irrigation status and indoor versus outdoor growing.

Utility

Plants produced by the Clean Stock® micropropagation systems and methods described herein provide improvements over current methods for cannabis propagation. Such improvements include but are not limited to maintenance of cultivars characteristics, production of large numbers of genetically identical plants, increased yield, increased efficiency of production in terms of time and space requirements, and disease-free plants that are not treated with pesticides.

In the Summary, the Detailed Description, the Claims, and the accompanying drawing, reference is made to particular features of the disclosure. These features can for example be components, ingredients, elements, devices, apparatus, systems, groups, ranges, method steps, test results and instructions, including program instructions.

It is to be understood that the disclosure of the invention in this specification does not include all possible combinations of such particular features. For example, where a particular feature is disclosed in the context of a particular aspect or embodiment of the invention, or a particular claim, or a particular figure, that feature can also be used in combination with and/or in the context of other particular aspects, embodiments, claims and figures, and in the invention generally, except where the context excludes that possibility.

The invention disclosed herein, and the claims, include embodiments not specifically described herein and can for example make use of features which are not specifically described herein, but which provide functions which are the same, equivalent or similar to, features specifically disclosed herein.

The term "comprises", and grammatical equivalents thereof are used herein to mean that, in addition to the features specifically identified, other features are optionally present. For example, a composition or device "comprising" (or "which comprises") components A, B and C can contain not only components A, B and C but also one or more other components.

When a range is given as "(a first number) to (a second number)" or "(a first number)–(a second number)", this means a range whose lower limit is the first number and whose upper limit is the second number. For example, "from 8 to 20 plants" or "8-20 plants" means a range whose lower limit is 8 plants, and whose upper limit is 20 plants. The terms "plural", "multiple", "plurality" and "multiplicity" are used herein to denote two or more than two features.

Where reference is made herein to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps, except where the context excludes that possibility.

Where reference is made herein to "first" and "second" features, this is generally done for identification purposes; unless the context requires otherwise, the first and second features can be the same or different, and reference to a first feature does not mean that a second feature is necessarily present (though it may be present).

Where reference is made herein to "a" or "an" feature, this includes the possibility that there are two or more such features (except where the context excludes that possibility). Thus, there may be a single such feature or a plurality of such features. Where reference is made herein to two or more features, this includes the possibility that the two or more features are replaced by a lesser number or greater number of features which provide the same function, except where the context excludes that possibility.

The term "and/or" is used herein to mean the presence of either or both of the two possibilities stated before and after "and/or". The possibilities can for example be components, ingredients, elements, devices, apparatus, systems, groups, ranges and steps) is present. For example, "item A and/or item B" discloses three possibilities, namely (1) only item A is present, (2) only item B is present, and (3) both item A and item B are present.

Where this specification refers to a component "selected from the group consisting of" two or more specified sub-components, the selected component can be a single one of the specified sub-components or a mixture of two or more of the specified sub-components.

What is claimed is:

1. A system for in vitro propagation of disease-free clonal cannabis plants, comprising:
    (a) a clean explant from a mother cannabis plant maintained in a vegetative state throughout its life, wherein the mother cannabis plant is a virus-tested and culture-indexed mother cannabis plant;
    (b) aseptic tissue culture media for propagation of the clean explant, wherein the tissue culture media comprises Driver and Kuniyaki Walnut (DKW) media and no hormones;
    (c) an incubator for propagation of the clean explant comprising conditions effective to produce disease-free cannabis plants; and
    (d) disease-free clonal cannabis plants.

2. The system of claim 1, wherein the clean explant is one or more of meristematic tissue, an apical explant, a nodal explant, root tips, shoot tips, young stems and young leaves.

3. The system of claim 1, wherein said conditions effective to produce disease-free cannabis plants comprise an incubator with controlled light intensity, photoperiod, temperature and humidity.

4. A method for in vitro propagation of disease-free clonal cannabis plants, comprising:
    (a) obtaining a clean explant from a mother cannabis plant;
    (b) placing the clean explant on tissue culture media under aseptic conditions on day 0, wherein the tissue culture media comprises Driver and Kuniyaki Walnut (DKW) media and no hormones; and
    (c) micropropagating the clean explant to produce disease-free clonal cannabis plants, wherein within 15 to 17 weeks following day 0, the number of clonal disease-free cannabis plants produced is at least 200 times (200×), at least 210 times (210×), at least 220 times (220×), at least 230 times (230×), at least 240 times (240×), at least 250 times (250×), or at least 256 times (256×) the number of starting clean explants, or
    (c') micropropagating the clean explant to produce disease-free clonal cannabis plants, wherein within 15 to 17 weeks following day 0, the number of clonal disease-free cannabis plants produced is at least 1000 times (1000×), at least 2000 times (2000×), at least 3000 times (3000×), at least 4000 times (4000×), at least 4020 times (4020×), at least 4040 times (4040×), at least 4060 times (4060×), at least 4080 times (4080×), or at least 4096 times (4096×) the number of starting clean explants.

5. The method of claim 4, wherein within 15 to 17 weeks following day 0, the method is effective to produce a number of disease-free clonal cannabis plants selected from the group consisting of, 30 to 1536 clonal disease-free cannabis plants when tissue culture is initiated with 6 clean explants, 45 to 2304 clonal disease-free cannabis plants when tissue culture is initiated with 9 clean explants, and 60 to 3072 clonal disease-free cannabis plants when tissue culture is initiated with 12 clean explants.

6. The method of claim 4, wherein the clean explant is one or more of meristematic tissue, an apical explant, a nodal explant, root tips, shoot tips, young stems and young leaves.

7. The method of claim 4, wherein the mother cannabis plant is a virus-tested and culture-indexed mother plant.

8. The method of claim 4, wherein the disease-free clonal cannabis plants are true-to-type and have the chemotype of a marijuana cultivar.

9. The method of claim 4, wherein the disease-free clonal cannabis plants are true-to-type and have the chemotype of a hemp cultivar.

10. The method of claim 4, wherein within 15 to 17 weeks following day 0, the method is effective to produce a number of disease-free clonal cannabis plants selected from the group consisting of 30 to 24576 clonal disease-free cannabis plants when tissue culture is initiated with 6 clean explants, 45 to 36864 clonal disease-free cannabis plants when tissue culture is initiated with 9 clean explants, and 60 to 49152 clonal disease-free cannabis plants when tissue culture is initiated with 12 clean explants.

11. A method of producing true-to-type disease-free clonal cannabis plants by micropropagation of an explant from a mother cannabis plant, comprising:
    (a) initiating tissue culture from an explant of a mother cannabis plant;
    (b) performing culture indexing;
    (c) micropropagating the explant;
    (d) pre-rooting or rooting the explant; and
    (e) acclimatizing the explant, wherein the method is effective to produce a number of disease-free clonal cannabis plants that is at least 200 times (200×) the number of starting explants within 15 to 17 weeks of initiation of the culture, and wherein the method comprises culturing the explants with tissue culture media comprising Driver and Kuniyaki Walnut (DKW) media and no hormones.

12. The method of claim 11, wherein the explant is one or more of meristematic tissue, an apical explant, a nodal explant, root tips, shoot tips, young stems and young leaves.

13. The method of claim 11, wherein performing culture indexing comprises placing the explant into aseptic culture broth and screening the broth for bacteria and fungi.

* * * * *